United States Patent
Meglan

(10) Patent No.: US 11,123,149 B2
(45) Date of Patent: Sep. 21, 2021

(54) METHODS OF USING AN ANGLED ENDOSCOPE FOR VISUALIZING A BODY CAVITY WITH ROBOTIC SURGICAL SYSTEMS

(71) Applicant: Covidien LP, Mansfield, MA (US)

(72) Inventor: Dwight Meglan, Westwood, MA (US)

(73) Assignee: COVIDIEN LP, Mansfield, MA (US)

( * ) Notice: Subject to any disclaimer, the term of this patent is extended or adjusted under 35 U.S.C. 154(b) by 322 days.

(21) Appl. No.: 15/765,866

(22) PCT Filed: Oct. 5, 2016

(86) PCT No.: PCT/US2016/055396
§ 371 (c)(1),
(2) Date: Apr. 4, 2018

(87) PCT Pub. No.: WO2017/062393
PCT Pub. Date: Apr. 13, 2017

(65) Prior Publication Data
US 2018/0280110 A1 Oct. 4, 2018

Related U.S. Application Data

(60) Provisional application No. 62/239,412, filed on Oct. 9, 2015.

(51) Int. Cl.
*A61B 34/30* (2016.01)
*A61B 90/00* (2016.01)
(Continued)

(52) U.S. Cl.
CPC ............ *A61B 90/37* (2016.02); *A61B 1/0005* (2013.01); *A61B 1/00006* (2013.01);
(Continued)

(58) Field of Classification Search
CPC ......... A61B 90/37; A61B 35/20; A61B 34/30; A61B 34/37; A61B 1/00006;
(Continued)

(56) References Cited

U.S. PATENT DOCUMENTS 4,248,213 A 2/1981 Landre
5,159,446 A 10/1992 Hibino et al.
(Continued)

FOREIGN PATENT DOCUMENTS

JP H08332169 A 12/1996
JP 2014095953 A 5/2014
(Continued)

OTHER PUBLICATIONS

Partial Supplementary European Search Report corresponding to counterpart Patent Application EP 16854185.2 dated May 10, 2019.
(Continued)

*Primary Examiner* — Christopher L Cook
*Assistant Examiner* — Brooke Lyn Klein

(57) ABSTRACT

A method of visualizing a body cavity during a surgical procedure including positioning an elongated body of an angled endoscope in a first position within a body cavity of a patient, rotating the elongated body about a longitudinal axis in response to a command point, capturing a plurality of images with an image capture device positioned within the elongated body as the elongated body is rotated, and generating a panoramic view of the body cavity from the plurality of images. In the first position of the elongated body, a surgical site is within a field of view of the image capture device. The field of view of the image capture device capturing a first volume of the body cavity, including the surgical site, when the angled endoscope is in the first position.

16 Claims, 6 Drawing Sheets

(51) Int. Cl.
*A61B 1/00* (2006.01)
*A61B 34/20* (2016.01)
*A61B 34/37* (2016.01)
*A61B 1/045* (2006.01)

(52) U.S. Cl.
CPC ...... *A61B 1/00009* (2013.01); *A61B 1/00048* (2013.01); *A61B 1/00149* (2013.01); *A61B 1/00174* (2013.01); *A61B 1/00179* (2013.01); *A61B 1/045* (2013.01); *A61B 34/20* (2016.02); *A61B 34/30* (2016.02); *A61B 34/37* (2016.02); *A61B 2034/2048* (2016.02); *A61B 2090/367* (2016.02); *A61B 2090/372* (2016.02); *A61B 2090/373* (2016.02)

(58) Field of Classification Search
CPC ............ A61B 1/00009; A61B 1/00048; A61B 1/0005; A61B 1/00149; A61B 1/00174; A61B 1/00179; A61B 1/045; A61B 2034/2048; A61B 2090/367; A61B 2090/372; A61B 2090/373
See application file for complete search history.

(56) References Cited

U.S. PATENT DOCUMENTS

| | | | |
|---|---|---|---|
| 5,243,967 A | 9/1993 | Hibino | |
| 6,346,076 B1 | 2/2002 | Rovegno | |
| 6,522,906 B1* | 2/2003 | Salisbury, Jr. | A61B 1/313 600/102 |
| 6,537,029 B1 | 3/2003 | Chen-Lung et al. | |
| 6,817,976 B2 | 11/2004 | Rovegno | |
| 6,887,196 B2 | 5/2005 | Arai et al. | |
| 7,381,183 B2 | 6/2008 | Hale et al. | |
| 7,559,890 B2 | 7/2009 | Wallace et al. | |
| 7,744,528 B2 | 6/2010 | Wallace et al. | |
| 8,277,373 B2 | 10/2012 | Maahs et al. | |
| 8,360,964 B2 | 1/2013 | Ertas | |
| 9,895,143 B2 | 2/2018 | Inoue | |
| 10,278,782 B2 | 5/2019 | Jarc et al. | |
| 2002/0082612 A1* | 6/2002 | Moll | G09B 23/285 606/130 |
| 2004/0015049 A1 | 1/2004 | Zaar | |
| 2004/0210105 A1 | 10/2004 | Hale et al. | |
| 2006/0106283 A1 | 5/2006 | Wallace et al. | |
| 2006/0161048 A1 | 7/2006 | Squicciarini | |
| 2006/0178556 A1 | 8/2006 | Hasser et al. | |
| 2006/0252995 A1 | 11/2006 | Hoeg et al. | |
| 2009/0245600 A1 | 10/2009 | Hoffman et al. | |
| 2009/0248036 A1* | 10/2009 | Hoffman | A61B 1/045 606/130 |
| 2010/0249506 A1* | 9/2010 | Prisco | A61B 1/00059 600/117 |
| 2012/0289781 A1 | 11/2012 | Pandey | |
| 2013/0162776 A1 | 6/2013 | Noack | |
| 2014/0267626 A1* | 9/2014 | Lilagan | H04N 5/23216 348/46 |
| 2015/0351864 A1 | 12/2015 | Kamon et al. | |
| 2016/0213364 A1 | 7/2016 | Inoue | |
| 2016/0354166 A1* | 12/2016 | Popovic | A61B 1/3132 |
| 2017/0172675 A1* | 6/2017 | Jarc | G02B 27/0093 |
| 2017/0188792 A1* | 7/2017 | Itkowitz | A61B 90/00 |
| 2017/0231701 A1* | 8/2017 | Cohen | A61B 90/57 600/104 |
| 2017/0273549 A1* | 9/2017 | Nazareth | G06F 3/017 |
| 2018/0325604 A1* | 11/2018 | Atarot | A61B 5/1114 |

FOREIGN PATENT DOCUMENTS

| | | |
|---|---|---|
| WO | 2012001549 A1 | 1/2012 |
| WO | 2014104088 A1 | 7/2014 |
| WO | 2014121116 A2 | 8/2014 |
| WO | 2015121765 A1 | 8/2015 |
| WO | 2015142957 A1 | 9/2015 |

OTHER PUBLICATIONS

Extended European Search Report dated Aug. 16, 2019 corresponding to counterpart Patent Application EP 16854185.2.
Japanese Office Action dated Oct. 2, 2020 corresponding to counterpart Patent Application JP 2018-517288.
Notification of the First Office Action issued by the National Intellectual Property Administration of the People's Republic of China dated Jun. 16, 2020 in corresponding CN Patent Application No. 201680057733.6 with English translation.
Chinese Second Office Action dated Feb. 3, 2021 corresponding to counterpart Patent Application CN 201680057733.6.

* cited by examiner

METHODS OF USING AN ANGLED ENDOSCOPE FOR VISUALIZING A BODY CAVITY WITH ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2016/055396, filed Oct. 5, 2016, which claims the benefit of and priority to U.S. Provisional Patent Application Ser. No. 62/239,412, filed Oct. 9, 2015, the entire disclosure of which is incorporated by reference herein.

BACKGROUND

Robotic surgical systems have been used in minimally invasive medical procedures. During such a medical procedure, the robotic surgical system is controlled by a surgeon interfacing with a user interface. The user interface allows the surgeon to see and manipulate a tool that acts on a patient. The user interface includes a display and an input controller or handle that is moveable by the surgeon to control the robotic surgical system.

Generally, robotic surgical systems include an endoscope that is inserted through an opening of a patient to provide visualization of a surgical site within a body cavity of the patient. Current endoscopes provide a limited field of view of the surgical site. Specifically, the endoscope is directed to the surgical site where the tools are acting on tissue. This leaves a majority of the body cavity unobserved. During a medical procedure, there may be contact with non-target tissue within the body cavity that is outside the field of view of the endoscope (e.g., when tools are exchanged). As a result, observation of the non-target tissue may be desired or necessary.

During some medical procedures, multiple and/or specialized endoscopes are used to provide increased visualization of the body cavity. The use of multiple and/or specialized endoscopes may increase the cost of medical procedures. Further, the use of multiple endoscopes may require the endoscopes to be changed or swapped during a medical procedure. Additionally or alternatively, the use of multiple endoscopes may increase the number of openings required in the body cavity of the patient to provide visualization of the body cavity.

There is thus a need for a robotic surgical system that is capable of increasing visualization of a body cavity during a medical procedure utilizing a single endoscope.

SUMMARY

In an aspect of the present disclosure, a method of visualizing a body cavity during a surgical procedure includes positioning an elongated body of an angled endoscope in a first position within a body cavity of a patient, rotating the elongated body about the longitudinal axis in response to a command point, capturing a plurality of images with an image capture device as the elongated body is rotated, and generating a panoramic view of the body cavity from the plurality of images. Positioning the elongated body of the angled endoscope includes positioning a surgical site within a field of view of the image capture device. The image capture device positioned in a distal end portion of the elongated body. The field of view of the image capture device capturing a first volume of the body cavity which includes the surgical site when the angled endoscope is in the first position.

In aspects, the method includes translating the elongated body along a longitudinal axis that is defined by the elongated body away from the surgical site to a second position in response to the command point. The field of view of the image capture device at the second position may capture a second volume of the body cavity that is larger than the first volume. Rotating the elongated body about the longitudinal axis may occur when the elongated body is in the second position. The method may include returning the elongated body to the first position after generating the panoramic view of the body cavity.

In some aspects, the method includes initiating the command point or the method may include moving a surgical instrument within the body cavity such that the command point is initiated in response to movement of the surgical instrument. Moving the surgical instrument may include translating the surgical instrument into the body cavity. Alternatively, moving the surgical instrument may include translating the surgical instrument such that an end effector of the surgical instrument is withdrawn beyond a threshold distance from the surgical site. Withdrawing the end effector of the surgical instrument beyond the threshold distance may withdraw the end effector from the first volume. Moving the surgical instrument may include swapping the surgical instrument for a second surgical instrument.

In certain aspects, the method may include detecting an attribute of a clinician interfacing with a user interface of a robotic surgical system to initiate the command point. Detecting the attribute of the clinician interfacing with the user interface may include detecting a gaze of the clinician with the user interface and initiating the command point when the gaze of the clinician is not directed to a display of the user interface. Additionally or alternatively, detecting the attribute of the clinician interfacing with the user interface may include detecting movement of a portable display and initiating the command point based on predetermined movement of the portable display.

In particular aspects, rotating the surgical instrument includes pivoting the elongated body about a pitch axis orthogonal to the longitudinal axis. Additionally, rotating the surgical instrument may include pivoting the elongated body about a yaw axis that is orthogonal to the pitch axis and the longitudinal axis. The pitch, longitudinal, and yaw axes may intersect at a common pivot point.

In aspects, the method includes displaying the panoramic view on a wearable display such that movement of the wearable display updates a view of a clinician of the panoramic view. The method may include interacting with the panoramic view of the body cavity to adjust the panoramic view of the body cavity. Interacting with the panoramic view of the body cavity includes panning the panoramic view of the body cavity. Additionally or alternatively, interacting with the panoramic view of the body cavity includes zooming the panoramic view of the body cavity.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
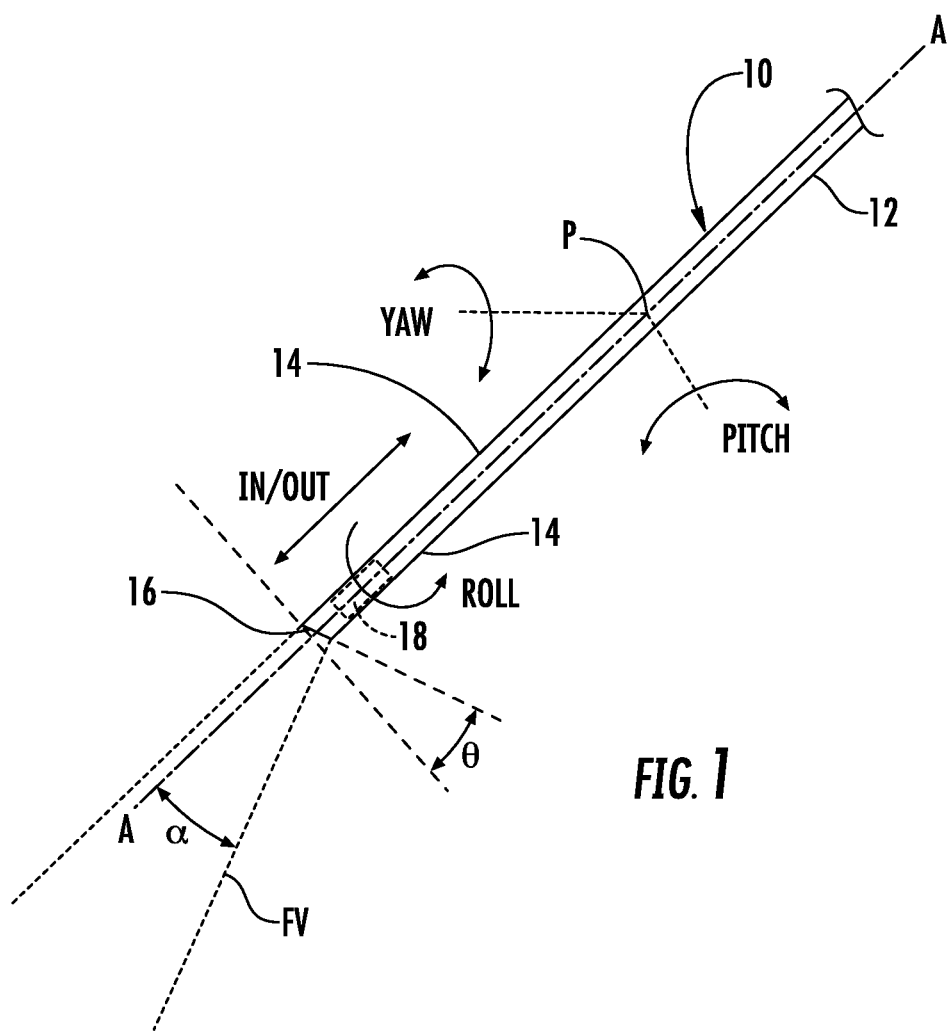
FIG. 1 is a schematic, side view of an endoscope provided in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Generally, this disclosure relates to methods and devices for visualizing a body cavity of a patient during a minimally invasive surgical procedure with an endoscope. Specifically, this disclosure details the use of an angled endoscope for use with a robotic surgical system that can function in the role of a 0° endoscope and provides panoramic views of a surgical site within a body cavity of a patient. As detailed below, the angled endoscope may be function as a 0° endoscope view of the surgical site where a tool is acting on tissue and may be repositionable to provide a panoramic view of the body cavity surrounding the surgical site. The angled endoscope may automatically provide such a panoramic view at a predetermined command point or time interval (e.g., at predetermined time intervals or at a particular step during the surgical procedure). Additionally or alternatively, the angled endoscope may provide such a panoramic view in response to a user generated command point (e.g., at the request of a clinician). The endoscope may be used as a standalone instrument or may be used as part of a robotic surgical system.

Referring now to FIG. 1, an angled endoscope 10 is provided in accordance with the present disclosure and includes an elongated body 12 that defines a longitudinal axis "A-A" of the angled endoscope 10. The elongated body 12 extends to a distal end portion 14 that includes an angled distal end 16 that defines an angle "O" from a line or plane that extends perpendicular to the longitudinal axis "A-A". As shown, the angle "O" is about 30°; however, the angle "O" may be in a range of about 0° to about 60°.

The angled endoscope 10 includes an image capture device 18 (e.g., a camera) that captures images of the body cavity "C" (FIG. 2) through the distal end 16 of the elongated body 12. The images may be in the form of still images or video. As shown, the image capture device 18 is positioned in the distal end portion 14 of the elongated body 12; however, it is contemplated that the image capture device 18 may be positioned anywhere within the elongated body 12. It is also contemplated that the image capture device 18 may be positioned outside of the elongated body 12 and may include a fiber optic cable (not shown) positioned within the elongated body 12 to capture images through the distal end 16 of the elongated body 12. The image capture device 18 has a conical field of view "FV" through the distal end 16 of the elongated body 12 such that one edge or a first edge of the field of view "FV" is approximately parallel to the longitudinal axis "A-A" and another, opposite, or second edge of the field of view "FV" extends at an angle "α" of approximately 30° with the longitudinal axis "A-A". It will be appreciated that for different angles "θ" the angle of the second edge of the field of view "FV" will also change.

Figure 2:
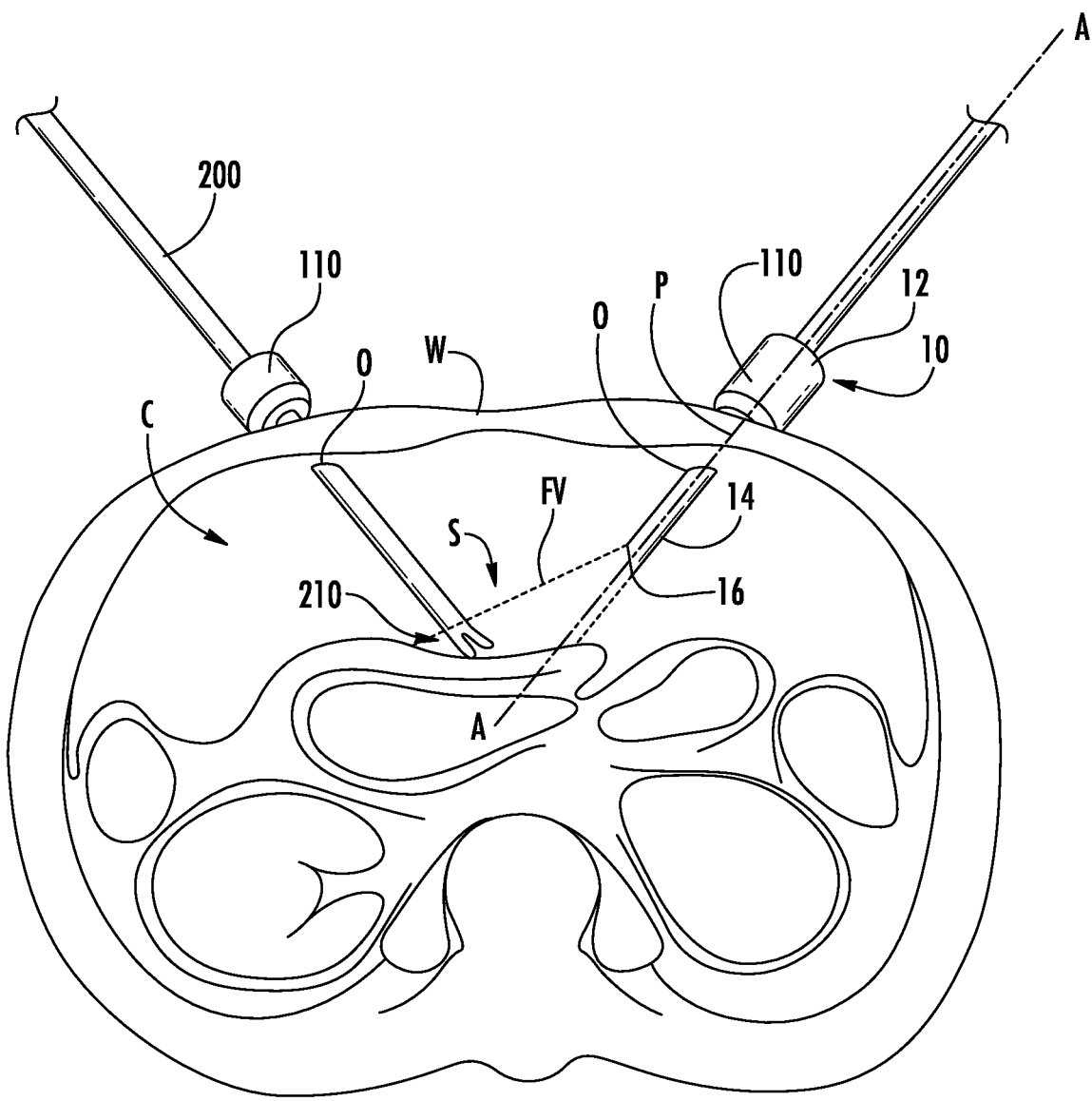
FIG. 2 is a cut-away view of a body cavity of a patient with the endoscope of FIG. 1 in a first position and a surgical instrument positioned at a surgical site within a field of view of the endoscope.

With additional reference to FIG. 2, the angled endoscope 10 is inserted through an opening "O" in a body cavity "C" of a patient for visualizing the body cavity "C" during a surgical procedure. The opening "O" may be a naturally occurring orifice or an incision. The angled endoscope 10 may be inserted through a cannula 110 that is positioned within the opening "O".

During a surgical procedure, the elongated body 12 is positioned such that the longitudinal axis "A-A" passes through the surgical site "S" such that the entire surgical site "S" is within the conical field of view "FV". With particular reference to FIG. 1, the angled endoscope 10 is moveable in at least four degrees of freedom to align the longitudinal axis "A-A" with the surgical site "S" and to view the body cavity with the image capture device 18. First, the elongated body 12 is translatable in and out along the longitudinal axis "A-A". Second, the elongated body 12 is rollable or rotatable about the longitudinal axis "A-A". Thirdly, the elongated body is pivotable about a pitch axis that intersects and is orthogonal to the longitudinal axis "A-A" at pivot point "P". Finally, the elongated body 12 is pivotable about a yaw axis that intersects and is orthogonal to the longitudinal axis "A-A" and orthogonal to the pitch axis at the pivot point "P". As shown in FIG. 2, the pivot point "P" is the point where the longitudinal axis "A-A" passes through a wall "W" defining the body cavity "C".

Continuing to refer to FIG. 2, during a surgical procedure, a surgical instrument 200 is inserted through an opening "O" in the wall "W" defining the body cavity "C". The surgical instrument 200 may be inserted through the same opening "O" as the angled endoscope 10 or through a different opening "O" as shown in FIG. 2. The surgical instrument 200 includes an end effector 210 to act on tissue of a patient at the surgical site "S". The elongated body 12 of the angled endoscope 10 is positioned to visualize a volume of the body cavity "C" such that surgical site "S" and the end effector 210 of the surgical instrument 200 are within the field of view "FV" of the image capture device 18. The elongated body 12 of the angled endoscope 10 is positioned such that the end effector 210 of the surgical instrument 200 and the surgical site "S" are within the field of view "FV" of the image capture device 18. The angled endoscope 10 may operate as a 0° endoscope to view the surgical site "S" by manipulating the elongated body 12 (e.g., pivoting the angled endoscope 10 about its yaw and pivot axes). It will be appreciated that as the distance between the image capture device 18 and the surgical site "S" is reduced, details of images of the surgical site "S" captured by the image capture device 18 is increased.

Figure 3:
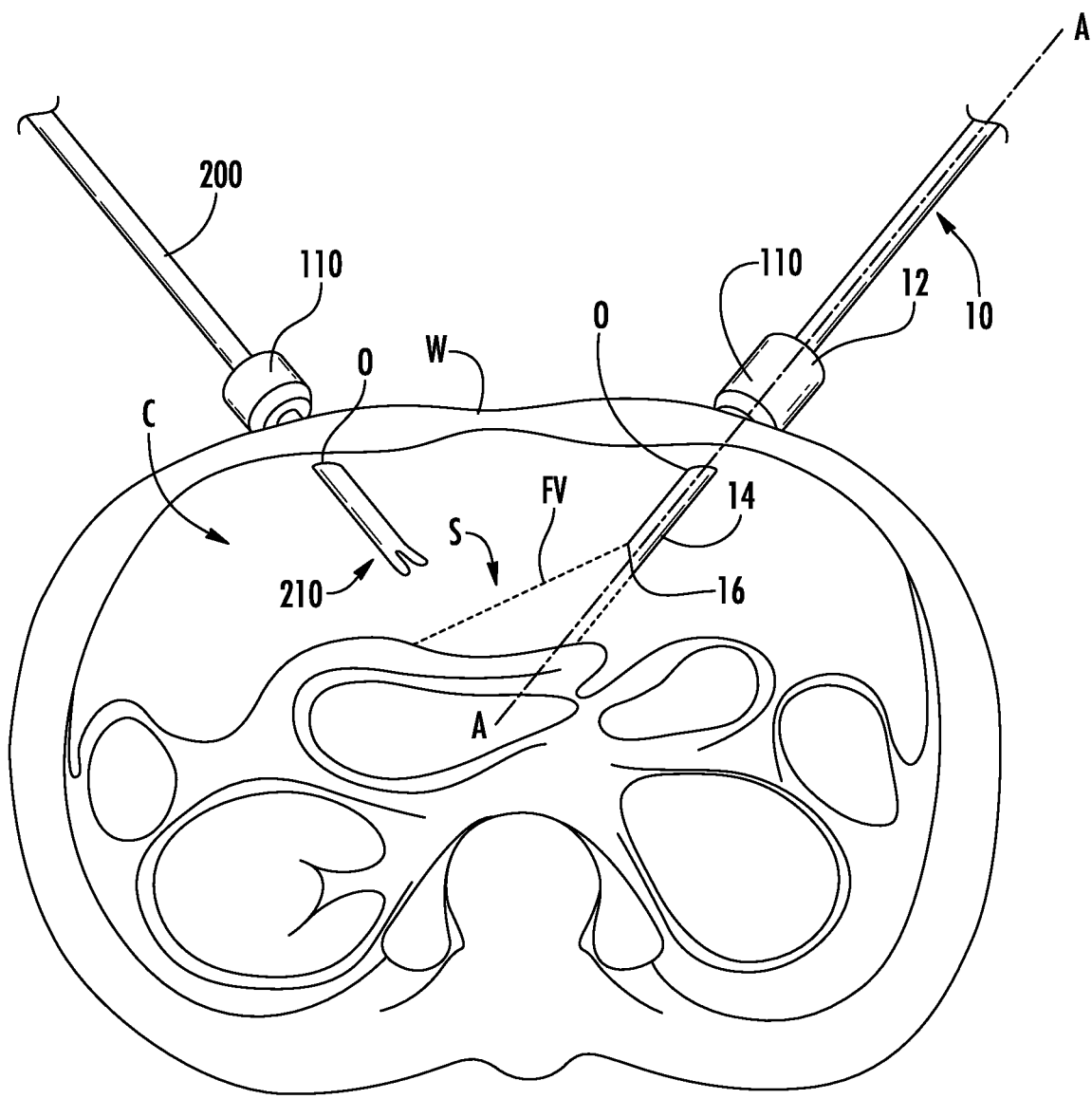
FIG. 3 is a cut-away view of the body cavity of the patient of FIG. 2 with the surgical instrument withdrawn from the field of view of the endoscope.

Referring to FIG. 3, during the surgical procedure the surgical instrument 200 may be withdrawn from the surgical site "S" or out of the body cavity "C" such that the end effector 210 of the surgical instrument 200 is withdrawn from the surgical site "S" and the field of view "FV" of the image capture device 18. The surgical instrument 200 may be withdrawn from the surgical site "S" for various reasons including, but not limited to, to swapping the surgical instrument 200 for another surgical instrument (not shown), to reloading the end effector 210, and repositioning the end effector 210. As the surgical instrument 200 is withdrawn from the field of view "FV", the surgical instrument 200 may contact tissue within the body cavity "C" outside of the field of view "FV" of the image capture device 18.

Figure 4:
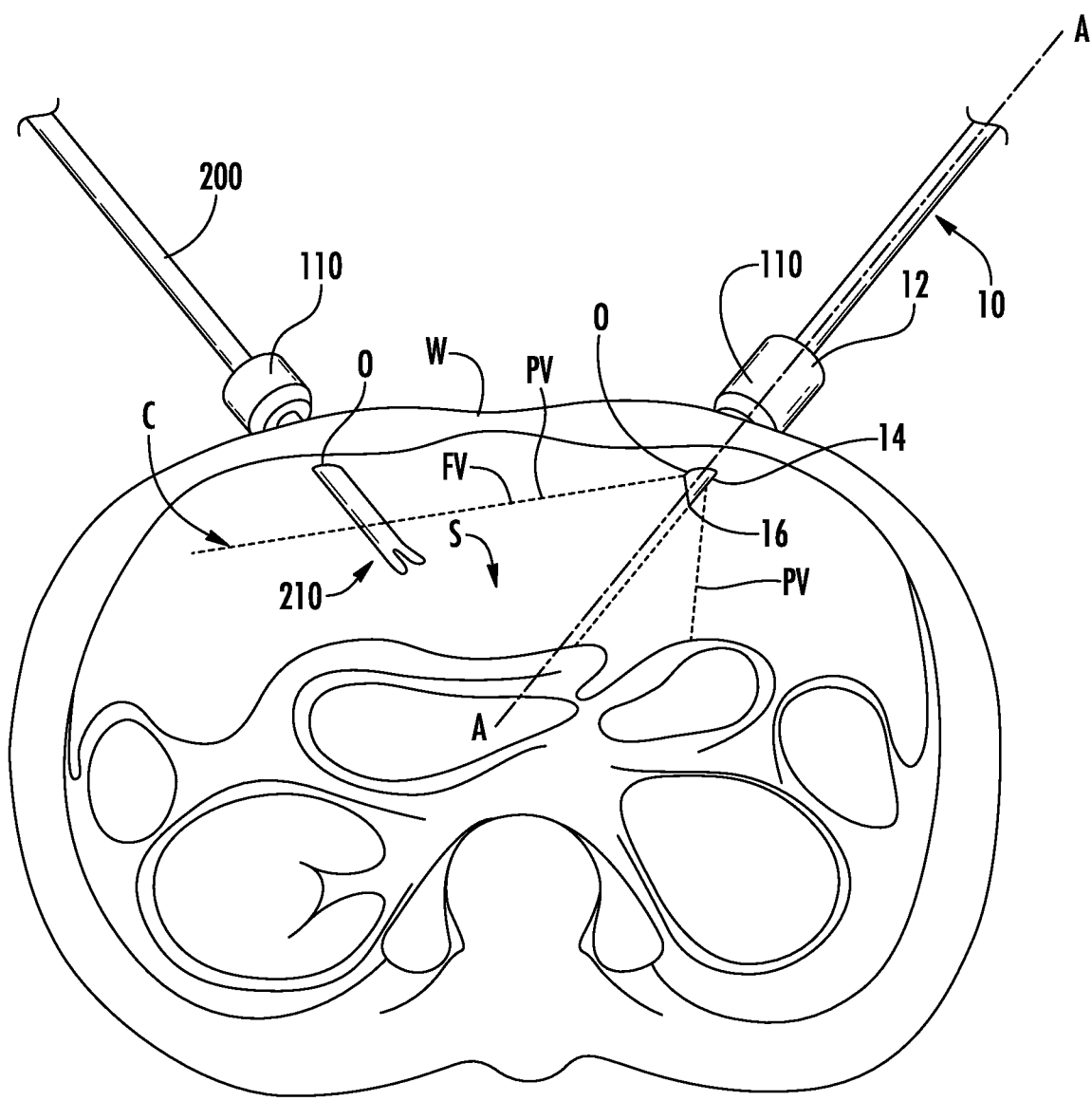
FIG. 4 is a cut-away view of the body cavity of the patient of FIG. 2 with the endoscope in a second position and with the surgical instrument recaptured in the field of view of the endoscope.

With reference to FIG. 4, the angled endoscope 10 may be translated out of the body cavity "C", along the longitudinal axis "A-A", such that the distal end 16 of the angled endoscope 10 is moved away from the surgical site "S". As the distal end 16 of the angled endoscope 10 is moved away from the surgical site "S", the field of view "FV" of the image capture device 18 encompasses a larger volume of the body cavity "C", wherein the end effector 210 of the surgical instrument 200 is within the field of view "FV" when the end effector 210 is withdrawn from the surgical site "S" while remaining within the body cavity "C" such that tissue surrounding the end effector 210 is within the field of view "FV" of the image capture device 18. In addition, the angled endoscope 10 may be rolled or rotated about the longitudinal axis "A-A" to capture a plurality of images within a panoramic field of view "PV" that includes the original field of view "FV". This panoramic field of view "PV" is a panoramic view of the surgical site "S" created by stitching together the plurality of images captured during the rolling or rotation of the angled endoscope 10. The panoramic field of view "PV" provides visualization of the body cavity "C" surrounding the surgical site "S" to allow a clinician greater visualization of the body cavity "C". It is contemplated that during the rolling or rotation of the angled endoscope 10, the angled endoscope 10 may also be pivoted about the pitch axis and/or the yaw axis (FIG. 1) to adjust a focal point of the image capture device 18, to increase the panoramic field of view "PV".

As detailed above, the rolling or rotation of the angled endoscope 10 about the longitudinal axis "A-A" is a full rotation of 360°; however, the rotation of the angled endoscope 10 may be a partial rotation of less than 360°. When the angled endoscope 10 is only partially rolled or rotated to generate a panoramic field of view "PV", the angled endoscope 10 may be rolled or rotated back to a pre-rotated position. It is contemplated that the full or partial rolling or rotation of the angled endoscope 10 has a duration of approximately 1.0 seconds; however, the full or partial rotation of the angled endoscope may have a duration of about 0.1 seconds to about 2.0 seconds.

The generation of a panoramic field of view "PV" may be initiated automatically at a predetermined command point or when a command point is initiated by a clinician. Some examples of a predetermined command point include, but are not limited to, when the end effector 210 is withdrawn from the surgical site "S", when a surgical instrument (e.g., surgical instrument 200) is inserted through an opening "O", when a surgical instrument is withdrawn from an opening "O", when a surgical instrument is withdrawn from the field of view "FV", or at time intervals.

Figure 5:
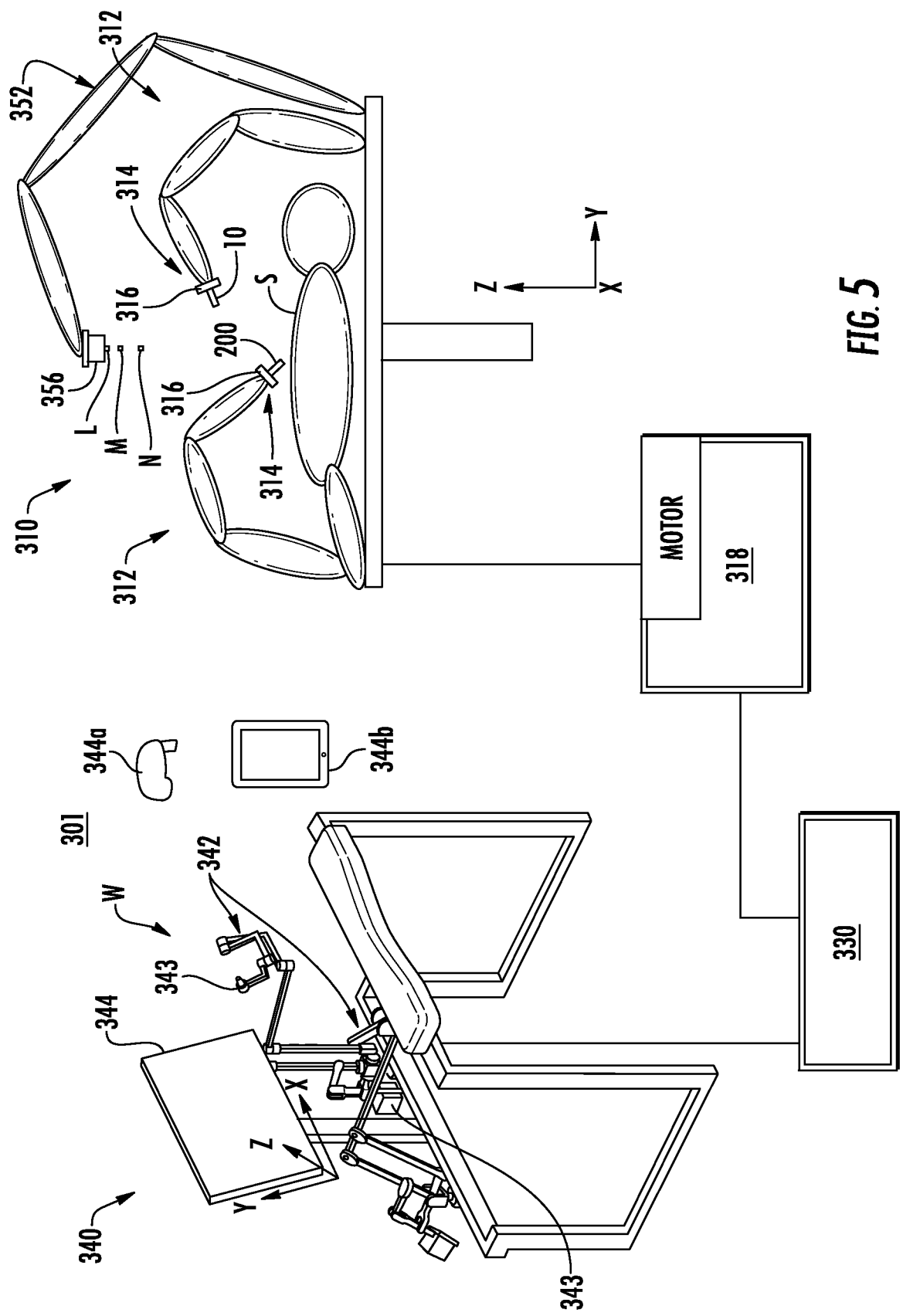
FIG. 5 is a schematic illustration of a user interface and a robotic system in accordance with the present disclosure.

Referring to FIG. 5, the angled endoscope 10 and the surgical instrument 200 may be part of a robotic surgical system 301 in accordance with the present disclosure. The robotic surgical system 301 includes a robotic system 310, a processing unit 330, and a user interface 340. The robotic system 310 generally includes linkages 312 and a robot base 318. The linkages 312 moveably support a tool (e.g., angled endoscope 10 or surgical instrument 200). The linkages 312 may be in the form of arms each having an end 314 that supports a tool. The user interface 340 is in communication with the robot base 318 through the processing unit 330.

The user interface 340 includes a display device 344 which is configured to display three-dimensional images. The display device 344 displays three-dimensional images of the surgical site "S" which may include data captured by imaging devices positioned on the ends 314 of the linkages 312 (e.g., angled endoscope 10) and/or include data captured by imaging devices that are positioned about the surgical theater (e.g., an imaging device positioned within the surgical site "S", an imaging device positioned adjacent the patient, imaging device 356 positioned at a distal end of an imaging arm 352). The imaging devices may capture visual images, infra-red images, ultrasound images, X-ray images, thermal images, and/or any other known real-time images of the surgical site "S". The imaging devices transmit captured imaging data to the processing unit 330 which creates three-dimensional images of the surgical site "S" in real-time from the imaging data and transmits the three-dimensional images to the display device 344 for display.

The user interface 340 also includes input arms or handles 342 which allow a clinician to manipulate the robotic system 310 (e.g., move the linkages 312, the ends 314 of the linkages 312, and/or the tools). Each of the input handles 342 is in communication with the processing unit 330 to transmit control signals thereto and to receive feedback signals therefrom. Each of the input handles 342 may include an input device which allow the surgeon to manipulate (e.g., clamp, grasp, fire, open, close, rotate, thrust, slice, etc.) the tools supported at the ends 314 of the linkages 312.

During a surgical procedure, the robot system 310 may operate the angled endoscope 10 to function as a 0° endoscope while a clinician is engaged with the user interface 340 by manipulating the linkages 312. When a clinician disengages from the user interface 340 (e.g., when the clinician releases the input handles 342, when the clinician looks away from the display 344) the user interface 340 may generate a command point such that the processing unit 330 sends a signal to the robot system 310 to generate a panoramic view of the surgical site "S" with the angled endoscope 10, as detailed above. Additionally, the robotic system 310 may use kinematic tracking to generate a command point when a tool (e.g., surgical instrument 200) completes a particular movement (e.g., when the tool is withdrawn beyond a threshold distance, when one tool is exchanged for another tool).

The user interface 340 then displays the panoramic view of the surgical site "S" on the display 344. As detailed above the display 344 may be a 3D display such that the panoramic view of the surgical site "S" is displayed in 3D. The display 344 may be an interactive display such that a clinician may pan, rotate, zoom in, and/or zoom out of areas of interest within the panoramic view of the surgical site. Additionally or alternatively, it is contemplated that the display 344 may include a display helmet 344a such that the movement of a head of clinician may allow a clinician to interact with the panoramic view of the surgical site "S". The helmet 344a may use inertial tracking to detect movement of the head of a clinician. Further, it is contemplated that the user interface 340 may include a portable display or monitor 344b that is moveable relative to the display 344. The portable display 344b displays a view of the surgical site "S" and may use inertia tracking to update the view of the surgical site "S" on the portable display 344b as the portable display 344b is moved relative to the display 344. In addition, a clinician may interact with the portable display 344b to update the view of the surgical site "S" on the portable display 344b. It is also contemplated that the portable display 344b may be used without the display 344.

Figure 6:
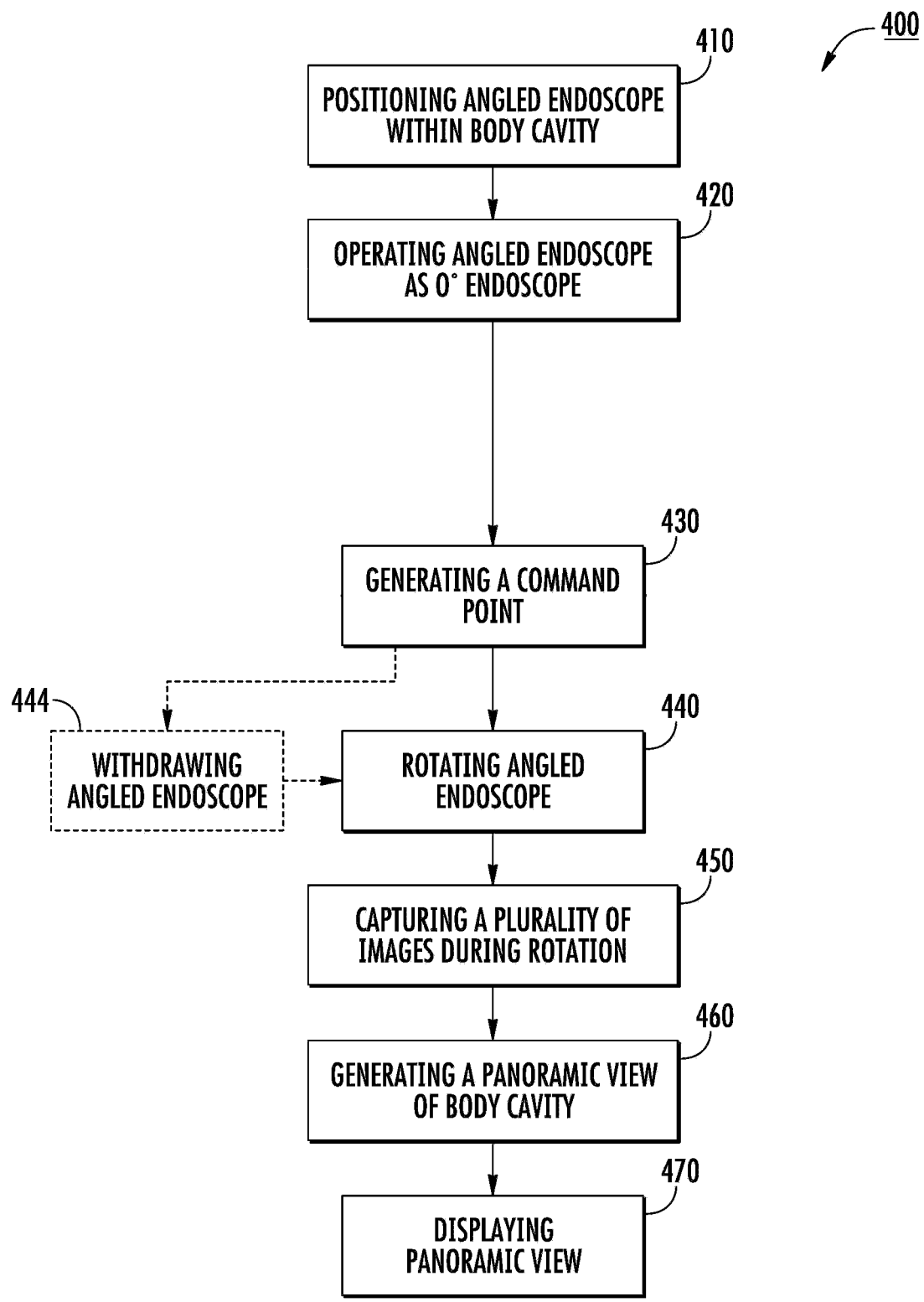
FIG. 6 is a flow diagram of a method of viewing a body cavity of a patient in accordance with the present disclosure.

Referring now to FIG. 6, a method 400 of visualizing a body cavity during a surgical procedure is described in accordance with the present disclosure utilizing an angled endoscope (e.g., angled endoscope 10). Initially, the angled endoscope is positioned within a body cavity "C" of a patient (Step 410). During the surgical procedure the angled endoscope may be operated as a 0° endoscope (Step 420). The angled endoscope may be operated as a 0° endoscope by manipulating the angled endoscope about its pitch, yaw, and longitudinal axes as detailed above.

During the surgical procedure, a command point is generated (Step 430). In response to the command point, the angled endoscope is rotated about is longitudinal axis (Step 440). The angled endoscope may be withdrawn within the body cavity "C" before the angled endoscope is rotated and returned to the position it had before being withdrawn after the angled endoscope is rotated (Step 444). As the angled endoscope is rotated, an image capture device 18) disposed within the angled endoscope captures a plurality of images (Step 450). A panoramic view of the body cavity "C" is generated from the plurality of images (Step 460). The panoramic view is displayed to a clinician as detailed above (Step 470). The clinician may interact with the panoramic view as detailed above.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of visualizing a body cavity during a surgical procedure, the method comprising:
   positioning an elongated body of an angled endoscope in a first position within a body cavity of a patient such that a surgical site is within a field of view of a camera positioned in a distal end portion of the elongated body, the field of view of the camera capturing a first volume of the body cavity, including the surgical site, when the angled endoscope is in the first position;
   moving a surgical instrument within the body cavity to cause the elongated body to be rotated about a longitudinal axis defined by the elongated body;
   capturing a plurality of images with the camera as the elongated body is rotated;
   generating a panoramic view of the body cavity from the plurality of images; and
   detecting an attribute of a clinician interfacing with a user interface of a robotic surgical system to cause the elongated body to be further rotated about the longitudinal axis,
   wherein detecting the attribute of the clinician interfacing with the user interface includes detecting hand contact of the clinician with the user interface and rotating the elongated body when the clinician is not in hand contact with the user interface.

2. The method according to claim 1, further comprising manually causing the elongated body to be rotated.

3. The method according to claim 1, wherein moving the surgical instrument includes translating the surgical instrument into the body cavity.

4. The method according to claim 1, wherein moving the surgical instrument includes translating the surgical instrument such that an end effector of the surgical instrument is withdrawn beyond a threshold distance from the surgical site.

5. The method according to claim 4, wherein withdrawing the end effector of the surgical instrument beyond the threshold distance withdraws the end effector from the first volume.

6. The method according to claim 1, wherein moving the surgical instrument includes swapping the surgical instrument for a second surgical instrument.

7. The method according to claim 1, wherein the user interface includes a portable display.

8. The method according to claim 1, wherein moving the surgical instrument within the body cavity further causes the elongated body to be pivoted at a pivot point, wherein the elongated body is pivotal about a pitch axis orthogonal to the longitudinal axis.

9. The method according to claim 8, wherein moving the surgical instrument within the body cavity further causes the elongated body to be pivoted at the pivot point, wherein the elongated body is pivotal about a yaw axis that is orthogonal to the pitch axis and the longitudinal axis, and
   wherein the pitch, longitudinal, and yaw axes intersect at the pivot point.

10. The method according to claim 1, further comprising displaying the panoramic view on a wearable display such that movement of the wearable display updates a view of a clinician of the panoramic view.

11. The method according to claim 1, further comprising interacting with the panoramic view of the body cavity to adjust the panoramic view of the body cavity.

12. The method according to claim 11, wherein interacting with the panoramic view of the body cavity includes panning the panoramic view of the body cavity.

13. The method according to claim 11, wherein interacting with the panoramic view of the body cavity includes zooming the panoramic view of the body cavity.

14. A method of visualizing a body cavity during a surgical procedure, the method comprising:
   positioning an elongated body of an angled endoscope in a first position within a body cavity of a patient such that a surgical site is within a field of view of a camera positioned in a distal end portion of the elongated body, the field of view of the camera capturing a first volume of the body cavity, including the surgical site, when the angled endoscope is in the first position;
   moving a surgical instrument within the body cavity to cause the elongated body to be translated along a longitudinal axis defined by the elongated body away from the surgical site to a second position such that the field of view of the camera captures a second volume of the body cavity larger than the first volume and to further cause the elongated body to be rotated about the longitudinal axis in the second position;
   capturing a plurality of images with the camera as the elongated body is rotated;
   generating a panoramic view of the body cavity from the plurality of images; and detecting an attribute of a clinician interfacing with a user interface of a robotic surgical system to cause the elongated body to be further rotated about the longitudinal axis, wherein detecting the attribute of the clinician interfacing with the user interface includes detecting hand contact of the clinician with the user interface and rotating the elongated body when the clinician is not in hand contact with the user interface.

15. The method according to claim 14, further comprising returning the elongated body to the first position after the panoramic view of the body cavity has been generated from the plurality of images.

16. A method of visualizing a body cavity during a surgical procedure, the method comprising:

positioning an elongated body of an angled endoscope in a first position within a body cavity of a patient such that a surgical site is within a field of view of a camera positioned in a distal end portion of the elongated body, the field of view of the camera capturing a first volume of the body cavity, including the surgical site, when the angled endoscope is in the first position;

moving a surgical instrument within the body cavity to cause the elongated body to be rotated about a longitudinal axis defined by the elongated body;

capturing a plurality of images with the camera as the elongated body is rotated;

generating a panoramic view of the body cavity from the plurality of images; and detecting an attribute of a clinician interfacing with a user interface of a robotic surgical system to cause the elongated body to be further rotated about the longitudinal axis, wherein detecting an attribute of a clinician interfacing with the user interface includes detecting a gaze of the clinician with the user interface and the elongated body is rotated when the gaze of the clinician is not directed to a display of the user interface.

\* \* \* \* \*